(12) United States Patent
Hassell

(10) Patent No.: US 7,763,474 B2
(45) Date of Patent: Jul. 27, 2010

(54) MULTI-PHASE FLUID SAMPLING METHOD AND APPARATUS

(75) Inventor: James Clyde Hassell, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 1156 days.

(21) Appl. No.: 10/538,394

(22) PCT Filed: Jan. 7, 2004

(86) PCT No.: PCT/US2004/000607

§ 371 (c)(1),
(2), (4) Date: Dec. 27, 2005

(87) PCT Pub. No.: WO2004/062783

PCT Pub. Date: Jul. 29, 2004

(65) Prior Publication Data

US 2006/0141637 A1   Jun. 29, 2006

(51) Int. Cl.
*G01N 1/22* (2006.01)
(52) U.S. Cl. .................. 436/181; 436/139; 436/140; 436/141; 436/142; 436/143
(58) Field of Classification Search .................. 436/38, 436/139–143, 174, 181; 73/60.11, 151
See application file for complete search history.

(56) References Cited

U.S. PATENT DOCUMENTS 3,133,437 A * 5/1964 Remke et al. ............... 73/61.44
3,135,113 A * 6/1964 Walker et al. ................. 73/200
5,190,103 A * 3/1993 Griston et al. ............... 166/303
5,470,749 A * 11/1995 Djabbarah et al. ............ 436/38
5,597,950 A * 1/1997 Mullen ....................... 73/60.11
7,140,238 B2 * 11/2006 Beauducel et al. ......... 73/61.41

OTHER PUBLICATIONS

Akopova et al. "Chromatographic determination of C1-C5 Hydrocarbons in water-cut oil". 1968. Chemistry and Technology of Fuels and Oils. vol. 4, No. 7, pp. 543-545.*

* cited by examiner

*Primary Examiner*—Yelena G Gakh
*Assistant Examiner*—David Weisz
(74) *Attorney, Agent, or Firm*—Abelman, Frayne & Schwab

(57) ABSTRACT

The invention provides a method for producing a homogenous sample of a pressurized fluid stream flowing in a pipeline, the fluid stream consisting of a majority component of hydrocarbon gas, the remainder consisting of one or more hydrocarbon liquids and water in the form of vapor, aerosols, droplets and/or liquid streams, the method includes the steps of: a. injecting one or more surface active agents into the fluid stream in an injection zone at a rate that is sufficient to form a uniform foam of the gas and the one or more hydrocarbon liquids and water components; b. mixing the one or more surface active agents with the fluid stream in a mixing zone to form a uniform foam composition flowing in the pipeline downstream of the mixing zone; c. withdrawing a portion of the foam composition from the pipeline at a sampling point; d. passing the portion of the foam composition withdrawn through a sampling loop; and e. removing a sample of predetermined volume of the foam composition from the sampling loop for analysis.

18 Claims, 2 Drawing Sheets

MULTI-PHASE FLUID SAMPLING METHOD AND APPARATUS

FIELD OF THE INVENTION

This invention relates to methods and apparatus for sampling a multi-phase fluid stream that includes hydrocarbon gas as the major component, and hydrocarbon liquid(s) and water in a minor proportion, the samples being used for analysis and reporting of the content of the stream, e.g., for custody transfer accounting purposes in a gas transmission pipeline, well production applications, including gas-liquid separation facilities, and various types of meters, including venturi and differential pressure ("DP") flow meters, wet gas meters, gas turbine and ultrasonic meters.

BACKGROUND OF THE INVENTION

Natural gas conveyed through gas transmission pipelines is typically accompanied by minor proportions of water vapor and one or more vaporized liquid hydrocarbons. While these minor proportions of the later components are liquids at ambient pressure and temperature, the prevailing conditions in the pipeline will keep these compounds in a vaporized state. To the extent that some of these minor components condense on the interior walls of the pipeline, they can be removed by appropriate knock-out traps. However, for the purposes of obtaining an accurate analysis of the content of the fluid stream, such as for certifying its BTU value in a custody transfer context, or determining what downstream treatments may be required for removing undesired water vapor and/or certain types of vaporized hydrocarbons in a process stream feeding a reactor, current analytical methods and apparatus are found to be lacking.

As used herein the term "phase" means a type of fluid that can exist in contact with other fluids in a vaporized gaseous state or in a liquid state. A "multi-phase" fluid is a fluid containing more than one phase, i.e., liquid and gas, and can include a fluid having two or more liquid phases and/or a combination of a gas phase with one or more liquid phases. As will be understood by one of ordinary skill in the art, a mixture of hydrocarbon liquids, natural gas vapors and water includes a discrete hydrocarbon liquid and a discrete water phase as well as a discrete vapor phase containing water and hydrocarbon gases.

As used herein, the term "multi-phase fluid" includes a stream comprising natural gas, hydrocarbon liquids in the form of a stream, and/or small discrete drops or droplets, vaporized hydrocarbon liquids, water in the form of a stream and/or droplets and water vapor.

It is common for a natural gas stream to contain multiple fluid phases. As will be understood by one of ordinary skill in the art, gas transmission pipelines can be subjected to extreme temperature swings, e.g., daytime to nighttime changes of 60° F., or more, when taken at the same geographical location, and similar changes associated along the length of a pipeline where the altitude and associated temperature varies in mountainous terrain, as well as with exposure to sunlight. In these circumstances, the content of the fluid stream at a given point can change from a 100% vapor composition as the containing pipeline reaches its highest temperature, to a significant dropout and formation of liquid droplets of hydrocarbon and water as the pipeline cools to its lowest temperature. As is well known in the art, significant difficulties are associated with obtaining truly representative samples of the fluid from pressurized pipelines and in providing the sample in a state that is analyzable by any of the number of known standard techniques.

These limitations represent a serious problem to the industry, since there are approximately 1.5 million natural gas wells worldwide, many of which produce a multi-phase fluid flow of natural gas, hydrocarbon liquids and water, called "wet gas". This condition is present in both raw well gas and in processed sales gas pipelines. In order for natural gas suppliers in some areas of the world to meet demand over the next ten to twenty years, it will be necessary to increase production from off-shore deep-water fields. Gas produced from such deep-water fields contains higher concentrations of low volatility components, including water vapor and heavy hydrocarbons that have a greater susceptibility to condense then gas from on-shore and off-shore shelf production areas.

During transmission or transport through pipelines, heavier gas components tend to condense out along the pipeline walls. Furthermore, when the fluid stream is sampled, additional condensation can occur due to the temperature and pressure differences between the mixture in the pipeline and in the sampling apparatus. Since the condensed components of the gas are commonly the heavy ends that are also rich in BTU content, these condensed components may never be analyzed because they cling to the walls of the equipment or drip back into the pipeline. Thus, the sample that is obtained where these conditions are prevalent is biased "lean", with the result that the BTU content of the gas flow in the pipeline is actually greater than that of the non-representative sample.

The BTU heating value of natural gas obviously has a significant impact on its monetary value. In general, the heating value of natural gas increases as the concentration of low volatility, high molecular weight components increases.

Mathematical models have been proposed, but none have been found that reliably predicts the flow regime of three-phase flowing fluids.

The American Petroleum Institute (API), International Standards Organization (ISO) and the Gas Processors Association (GPA) are among the leading industry organizations that have long recognized the problems and deficiencies in obtaining and analyzing representative samples. Currently, the petroleum industry has no suitable technology for extracting samples of a natural gas containing any form of liquid that is proportional to the liquid load of the source gas. These organizations have stated that the liquid phase should be removed from the source gas and measured separately.

One method recommended in the prior art literature utilizes a separator that is best suited for removal of liquid slugs and large droplets. Liquid aerosols, which are the most frequent source of liquid entrainment, are not easily separated from the sample gas by the proposed knock-out type of separator.

Another method teaches the heating of the sampling equipment to a temperature above the dew point of the components of the flowing gas while the sample is being taken. This approach proves impractical since electric power for heating is typically not available in the field at the pipeline sampling point. Condensation of gas phase components, which reduce the proportion of high molecular weight components, therefore tends to decrease gas phase heating value, while vaporization of entrained liquid has the opposite effect.

For custody transfer measurements, liquids entrained in natural gas are the source of many problems in sample conditioning systems. Since a small volume of liquid is equivalent to several hundred times its volume of gas, even microscopic amounts of hydrocarbon aerosol droplets can have a significant impact on gas composition and BTU value measurements.

The impact of poor and inaccurate sampling methods and apparatus also has a direct effect on flow measurement since typical measurement methodologies require the density of the fluid to determine the volumetric flow rate. Thus, in gas production operations, problems arise when a flow meter is used to measure rates in the combined multi-phase stream. Specifically, flow characteristics such as density in differential pressure change. These changing flow characteristics produce inaccurate readings in conventional metering devices. The accuracy of these measurements are particularly important to gas merchants and consumers, such as public and private utilities, since the liquid-gas composition of the fluid stream determines the royalties to be paid to the producers. This information also indicates how quickly a natural gas reservoir is being depleted. Multi-phase flow meters are designed to provide a direct measurement of the combined flowing fluid stream, but this measurement cannot be directly resolved into individual measurements of the respective phases.

It is known in the petroleum industry to use well test equipment to separate gas, gas liquids and water phases from the gas well flow stream. Test separators are expensive, occupy valuable space on production platforms and require a relatively long time to provide an accurate monitoring of a given well because of the stabilized flow pattern that is required. Additionally, it has been found that test separators are only moderately accurate, e.g., typically plus or minus 5-10% of each phase flow rate; these devices cannot be used for continuous flow monitoring.

Separation equipment used in the prior art has included large and bulky vessel-type separation devices that include a horizontal or vertically disposed oblong pressure vessel together with at least one internal valve and weir assembly. Industry terminology refers to a "two-phase" separator to describe separation of a gas phase from a liquid phase, the latter including oil and water. Such two-phase separators do not allow direct volumetric measurements of segregated oil and water components under actual producing conditions. A "three-phase" separator separates the gas from the liquid phases and further separates the liquid phase into oil and water phases. As compared to the two-phase separators, three-phase separators require additional valve and weir assemblies, as well as larger contained volumes to provide the longer residence times needed for separation of produced liquids.

A method of determining the quality of steam that mixes a surfactant with the steam to produce a stable foam is disclosed in U.S. Pat. No. 5,470,749. The foam is admitted to a capillary tube and a specific electrical measurement is obtained that can be related to steam quality by application of an algorithm. This patent also suggests that the method can be used for the purpose of determining the relative amounts of gas and liquid in a flowing multi-phase stream, where the liquids are non-conductive or only slightly conductive. However, no examples are provided for sampling and quality analysis except for steam. Importantly, the quality determination appears to be based upon calibration requirements, and no examples are provided for calculations relating to organic solvents and hydrocarbons.

A surfactant or surface-active agent, is any compound that reduces surface tension when dissolved in water or water solutions or which reduces interfacial tension between two liquids. The three generally recognized categories of surface active agents are detergents, wetting agents and emulsifiers. All three use the same basic chemical mechanism and differ chiefly in the nature of the surfaces involved. Detergents are classed as anionic, cationic or non-ionic, depending on their mode of chemical action. The non-ionic compounds function by a hydrogen bonding mechanism.

It is therefore one object of the present invention to provide apparatus and methods for accurately sampling and analyzing multi-phase fluids that overcome the problems of the prior art. In particular, it is an object of the present invention to provide apparatus and methods employing surface active foaming agents that are more accurate than those known to the prior art.

Another object of the invention is to provide an apparatus and methods that can be practiced at pipeline sampling points in the field where limited utilities and facilities are available to provide homogenized samples for direct testing or for recovery of samples in sample storage vessels that will be used to deliver the samples for analysis at a remote location.

A further specific object of the invention is to provide an improved apparatus that is skid-mounted and portable for use in field locations.

Yet another object of the invention is to provide an improved apparatus and method employing foaming agents in wet gas metering applications that is more accurate and economical than known techniques.

It is another object of the invention to provide an apparatus and method that can be used in place of prior art two-and three-phase test separators to obtain reliable and accurate multi-phase fluid flow measurements and for the reliable recovery of representative fluid samples from the flowing fluid stream.

Another object of the invention is to provide an apparatus and methods for sampling a flowing pressurized multi-phase fluid stream that will permit highly accurate measurements of the stream density, as well as the proportions of the various components in the mixture.

A further object of this invention is to provide a method and apparatus for moving a foam in a wet gas transmission pipeline and thereby enhance pump efficiency and energy savings.

Another object of the invention is to provide an improved method for applying a liquid corrosion inhibitor to pipe walls that will enhance corrosion inhibition in pipelines where water is present in the hydrocarbon stream.

SUMMARY OF THE INVENTION

The above objects and other advantages are provided by the method and apparatus of the invention in which a homogeneous sample of a pressurized multi-phase fluid stream flowing in a pipeline is obtained, the fluid stream consisting of a majority component of hydrocarbon gas, the remainder consisting of one or more hydrocarbon liquids and water in the form of vapor, droplets, aerosols and/or liquid streams, the method comprising:

a. injecting one or more surfactants, or surface active agents ("saa") into the fluid stream in an injection zone at a rate that is sufficient to form a uniform foam of the gas, one or more hydrocarbon liquids and water components;

b. mixing the one or more saa with the fluid stream in a mixing zone to form a uniform foam composition flowing in the pipeline downstream of the mixing zone;

c. withdrawing a portion of the foam composition from the pipeline at a sampling station; and d. collecting a sample of predetermined volume of the foam composition for analysis.

In one preferred embodiment, the surfactant addition is continuous. In another embodiment, the surfactant is injected intermittently, or pulsed, to coincide with coordinated intermittent sampling by an automated sample collection system or by an in-line analyzer. The intermittent injection method consumes less surfactant.

In one particularly preferred embodiment the surfactant is added in a surfactant injection zone and the mixture of the multi-phase fluid stream and surfactant enters a downstream mixing zone where the uniform stable homogeneous foam composition is formed. In an alternative preferred embodiment, the injection and mixing zones are combined with the surfactant being added in a region of high turbulence so that the mixing and creation of the homogeneous stable foam composition occurs without passing to a downstream mixing zone.

The surfactant is injected by any of several known means including metering pumps, pressurized or gravity-fed systems. Jets, nozzles and spray heads located in the flowing stream and/or positioned about the periphery of the pipeline can be employed.

The mixing can advantageously be completed in a separate mixing zone using static in-line mixes of the type that are well known in the art. Dynamic power mixers can also be employed to produce the uniform foam composition. Other known mixing means that can be utilized include screens, strainers, Y-strainers, pumps, and flow rate constrictions and variations, such as sudden changes in pipeline diameters The selection of one or a combination of mixing devices and means can be determined based on the flow profile of the liquid-gas. Slug flow can be accommodated by a Y-strainer, while highly turbulent flow can be created with a strainer.

Gas pipeline Y-strainers are used for mechanically removing solids from flowing liquids or gases by means of a perforated or wire mesh straining element. They are used in pipelines to protect equipment such as pumps, meters, control valves, steam traps, and regulators. Typically these strainers are dependent on pipeline size (2" or greater) and contain stainless steel screen sizes of 1/8" for gas/liquid applications (6 mesh). The same screen and sizing used for Y-strainers can be used for gas pipeline Tee-strainers and basket strainers.

Mixing efficiency can also be enhanced by reducing the cross-sectional area of the pipeline at the mixing zone to thereby increase the flow velocity and stream mixing. Determination of the optimum positioning for the sampling probe is required to insure that representative samples are obtained.

A sampling station is located downstream of the mixing zone where the stable homogeneous foam composition has been formed. A sampling probe with appropriate external piping for removal of a portion of the foam from the pipeline where sampling is intermittent, the initial portion of the sample is discarded to assure that a stable sampling state has been achieved. In one embodiment, the portion of the foam withdrawn from the pipeline is passed through a slipstream sampling loop and the sample is drawn from the sampling loop.

Foams can be tested for average bubble size and distribution to determine the degree to which homogenization has occurred. The nature of the surfactant, liquid viscosity, solid phase content, and mixing energy influence bubble size and distribution to a certain extent. Increased rotational speed of dynamic mixers is instrumental in decreasing bubble size; the size of bubbles exiting a porous medium is equal to the size of the pores. It is know that high-density foams produce diameters in the range of 150 to 800 microns when low viscosity liquid phases were foamed and high viscosity foams produced measured bubble diameters in the range of 60 to 465 microns.

It has also been determined static mixers generate mean bubble sizes in the range of 120 to 220 microns independent of foam density. Measurements of bubble size in low-density two, and three-phase foam and flow behavior of foam in pipes, where foam was generated by a static mixer, show that bubble diameters were between 100 and 1000 microns. No influence on foam density, bubble size or existence of solid particles on the flow behavior of the foam is apparent.

Foam fracturing fluid studies have shown that stable foams can be created with an average bubble diameter of 800 microns and a normal distribution range of from 400 to 1200 microns, indicating that homogenization has occurred.

Foam quality is measured by the percentage of gas trapped in the cells. A quality of 95% is considered the upper end of foam stability. Foams at a quality of 70% to 85% have effectively been used in reservoir formations to stimulate gas production. Foams having a quality value of 60% to 70% can be utilized in the practice of the invention.

Stable foams can be produced with an average bubble diameter of 800 microns, and a normal distribution range of from 400 to 1200 microns thus indicating that homogenization has occurred. A description of the bubble size distribution in foams is provided by den Engelsen, et al. in the AUTES Research Journal, Vol. 2, March 2002.

In a further preferred embodiment, the pipeline includes a defoaming zone downstream of the sampling zone. An appropriate defoaming compound or mixture is efficiently injected into the pipeline via jets, a quill and/or nozzles to break the foam.

The type of surfactants employed in the practice of the invention, as well as the quantities to be injected into the flowing multi-phase fluid stream are within the skill of the art. Surfactants of the anionic, cationic, amphoteric and non-ionic types can be utilized.

As will be understood by one of ordinary skill in the art, the composition of the multi-phase fluid stream to be analyzed will vary from one geographical location to another, from well to well, and even within the production stream from the same well. The surfactant type or types used in the practice of the invention will therefore be selected based upon the composition of the fluid stream.

The literature includes numerous reports of surfactants that are suitable for forming effective foams in various multi-phase fluid streams that provide functional foams in various hydrocarbon medice that also comprise salt and fresh water, condensates carbon dioxide and nitrogen. For example, the Society of Petroleum Engineers has published numerous technical papers reporting the results of tests of a wide variety of hydrocarbon, fluorochemical and fluorocarbon surfactants, including cationic, anionic, amphoteric and nonionic types.

The following publications issued by the society of Petroleum Engineers describe the function and selection of a wide variety of surfactant compositions for use with various fluid mixtures:

| 1. | SPE14394 | Surfactants for $CO_2$ Foam Flooding |
| 2. | SPE 30642 | A comparison of Mixed-Gas Foams with N2 |
| 3. | SPE 12785 | Laboratory Study of Foaming Surfactants as Steam Diverting Additives |
| 4. | SPE 7894 | The Use of Fluorochemical Surfactants in Non-Aqueous Stimulation Fluids |

-continued

| 5. | SPE 9008 | Water Soluble Fluorochemical Surfactant Well Stimulation Additives |
|---|---|---|
| 6. | SPE 9033 | Foamed Hydrocarbon |
| 7. | SPE 35600 | High-Quality Foam Fracturing Fluids |
| 8. | SPE 25168 | Polymer-Enhanced Foam: Laboratory Development and Evaluation |
| 9. | SPE 80242 | A Circulating Foam Loop for Evaluating Foam at Conditions of Use |
| 10. | SPE 75180 | Optimal Injection Strategies to Foam IOR |

The disclosures of these publications are incorporated herein by reference.

The following classes of surfactants can be utilized in the practice of the invention: alkyl sulfonates, including linear $C_{16-18}$ alpha-olefin sulfonate; alkyl aromatic sulfonates; di-sulfonates; alkyl and alkyl-aryl sulfonates including $C_{15-18}$ alkyl-toluene sulfonates; fluorocarbon/hydrocarbon blends; fluorinated alkyl esters; alcohol sulfates; alcohol ether sulfates; alcohol ethoxylate having $C_{9-11}$, $C_{12-15}$, $C_{12-13}$, and $C_{14-15}$ alkyl groups; alcohol ethoxyglycerl sulfonate having $C_{9-11}$ and $C_{12-15}$ groups; octylphenol ethoxyethyl sulfonate with a $C_8$ alkyl group; nonylphenol ethoxyacetate with a $C_9$ alkyl group; carboxymethylhydroxy propyl/guar polymer gel; ethoxylated alcohols; ethoxylated sulfates, including their sodium and ammonium salts; ethoxylated nonylphenols; ethoxylated alkyl phenols; alkanolamides; ethoxylated fatty acids; glycerol ester hydrotropes; amine oxides; lauryl sulfates; mono- and diglycerides; betaine-derived compounds; phosphate esters; quaternnary compounds; sorbitan derivatives; dodecylbenzene sulfonic acid; perfluoro compounds; perfluorooctanylbutane sulfonate; and mixtures of these compounds.

The one or more surfactants can be injected separately by metering pumps that are directed by a general purpose computer program and intermediate controller, the type and amounts being based upon the nature of the various components forming the multi-phase fluid stream, as well as the flow regime. The surfactants can be stored in separate containers connected by piping to the metering pump or pumps. Where the composition of the stream is known to be relatively consistent, an appropriate mixture of surfactants can be injected as a single stream in order to simplify the apparatus and necessary mixing means.

In the embodiment employing a dynamic mixing injector, a circulation loop is preferably installed to remove a portion of the fluid stream to the exterior of the pipeline, where a predetermined quantity of surfactant composition is added via a metering pump and the mixture is then returned by the sidestream carrying the surfactant to the interior of the pipeline via an appropriate set of jets and/or nozzles to assure turbulent mixing, thereby forming the homogeneous foam composition for subsequent sampling.

The invention provides improved sampling methods and apparatus, as well as more accurate analytical results for use in petrochemical plants, refineries, gas separation plants, natural gas pipelines and the like. The system can be used with in-line analyzers that provide real-time compositional data and for regular monitoring of the flowing fluid's composition. Alternatively, the invention can be used in conjunction with the filling of gas sample cylinders for laboratory or other remote location analysis of the collected samples. In the latter case, the sample container should be heated to approximately 20° F. above the temperature of the pipeline fluid at the point of sampling. Automated sampling and analysis system can also be utilized, where the introduction of the surfactant(s) occurs according to a predetermined schedule and the data from the completed analysis is transmitted via land lines, radio or satellite communications to a monitoring station at a remote laboratory. Power for the automated system can be provided by solar power collectors and batteries if electric transmission power lines are not available. The processor and controller can be provided on a programmed integrated circuit device.

In an especially preferred embodiment of the invention, the method is conducted utilizing a portable apparatus mounted or a skid, truck body, trailer, or the like. Portability allows the same apparatus to be utilized at well heads and custody transfer locations. A portable or skid-mounted apparatus will also facilitate the relocation of the equipment when a well is taken out of production. Pipe fittings are adapted for mating with standard well head, custody transfer and other sampling fittings and ports for ease and rapid installation of the apparatus of the invention. The portable system includes a test spool using an optimized length of pipe for foam generation in the field.

The specific configuration of the portable unit is determined by the particular application or applications, as well as the standards, particular type and arrangement of fittings, sample ports and the like customarily employed in a given country or geographical region The selection and particular configuration of the fittings and arrangement of the elements on the portable unit are well within the routine skill in the art, in view of the drawings and description of the invention provided herein.

In the practice of the invention on a well that has recently been brought into production, preliminary samples of the multi-phase fluid stream are analyzed to provide a baseline for selection of the one or more surfactants that will produce the desired foam stability. The surfactant(s) selected will also be based on the particular application, the nature of the sampling regime, e.g., continuous versus intermittent; whether the foam will be analyzed on-line or collected in a storage container for testing at a remote location; the cost of the surfactant(s); whether the foam will be broken in a downstream de-foaming zone or allowed to move through the transmission pipeline, and the like. For example, if the foam condition is to be maintained for an extended period of time for the purpose of transporting the mixture through the pipeline and pumping stations, foam stability and bubble size can be more important than for the application where the foam is removed from the pipeline, subjected to immediate analysis and the remaining foam broken in a downstream de-foaming zone.

As will also be apparent, the economics associated with the use of the surfactant(s) employed is a consideration in the practice of the invention. The cost of surfactants can be a significant practical factor. The use of an expensive surfactant that produces a desired type of foam in a given multi-phase product stream may only be practical for intermittent sampling applications where only a relatively small amount of the surfactant is needed to complete the sampling for analysis.

The factors mentioned above, and others, are to be considered in each specific application of the invention, which include, for example:
 1. custody transfer where potentially lost BTU values are accounted for at the point of sale;
 2. oil separation determinations in wet gas production;
 3. real-time determination of gas stream value in wet gas production;
 4. improved wet gas meter efficiency and accuracy;
 5. beneficial improvements in pumping efficiency in transmission pipelines; and 6. enhanced corrosion protection by movement of foam plugs through a pipeline.

BRIEF DESCRIPTION OF THE DRAWINGS

The method and apparatus of the invention will be described in further detail below and with reference to the attached drawing sheets in which.

DESCRIPTION OF THE PREFERRED EMBODIMENTS

Figure 1:
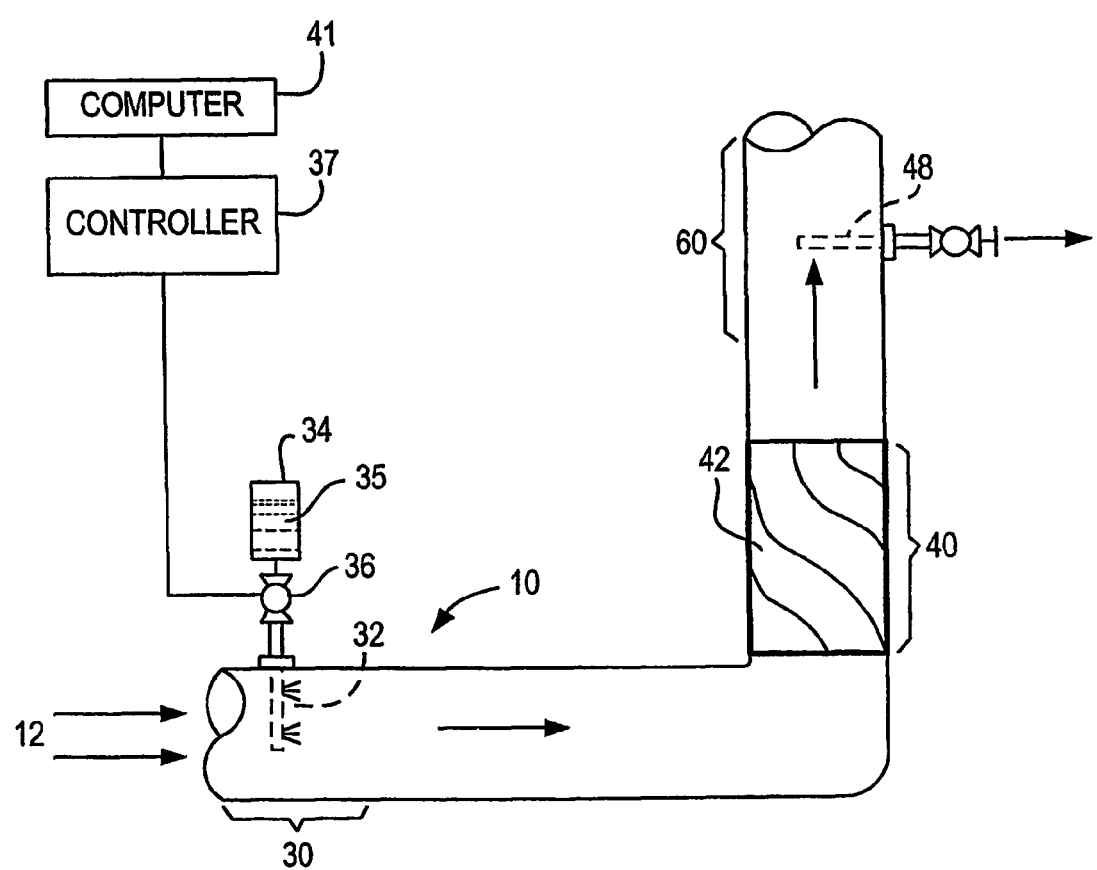
FIG. 1 is a schematic illustration of a first preferred embodiment of the invention.

Referring to FIG. 1, there is shown a portion of a gas transmission pipeline 10 that has been provided with one embodiment of the apparatus 20 of the invention. A surfactant injection zone 30 includes one or more liquid surfactant injection jets, quills or nozzles 32 in fluid communication with surfactant storage containers 34 and metering pumps 36. The amount of surfactant 35 to be added to the fluid stream 12 is determined based on a number of parameters, including the operating pressure and temperature of the fluid, the type and approximate amount of hydrocarbon liquids and water present.

The metering pumps 36 can be manually activated. In a preferred embodiment, a controller 37 directed by a programmed general purpose computer 41 actuates the flow of surfactant through the nozzles 32. These variables will be generally known to the operator of the pipeline and one of ordinary skill in the art will be able to determine the type and rate of addition of the one or more surfactants that will produce a stable and uniform stream.

Figure 2:
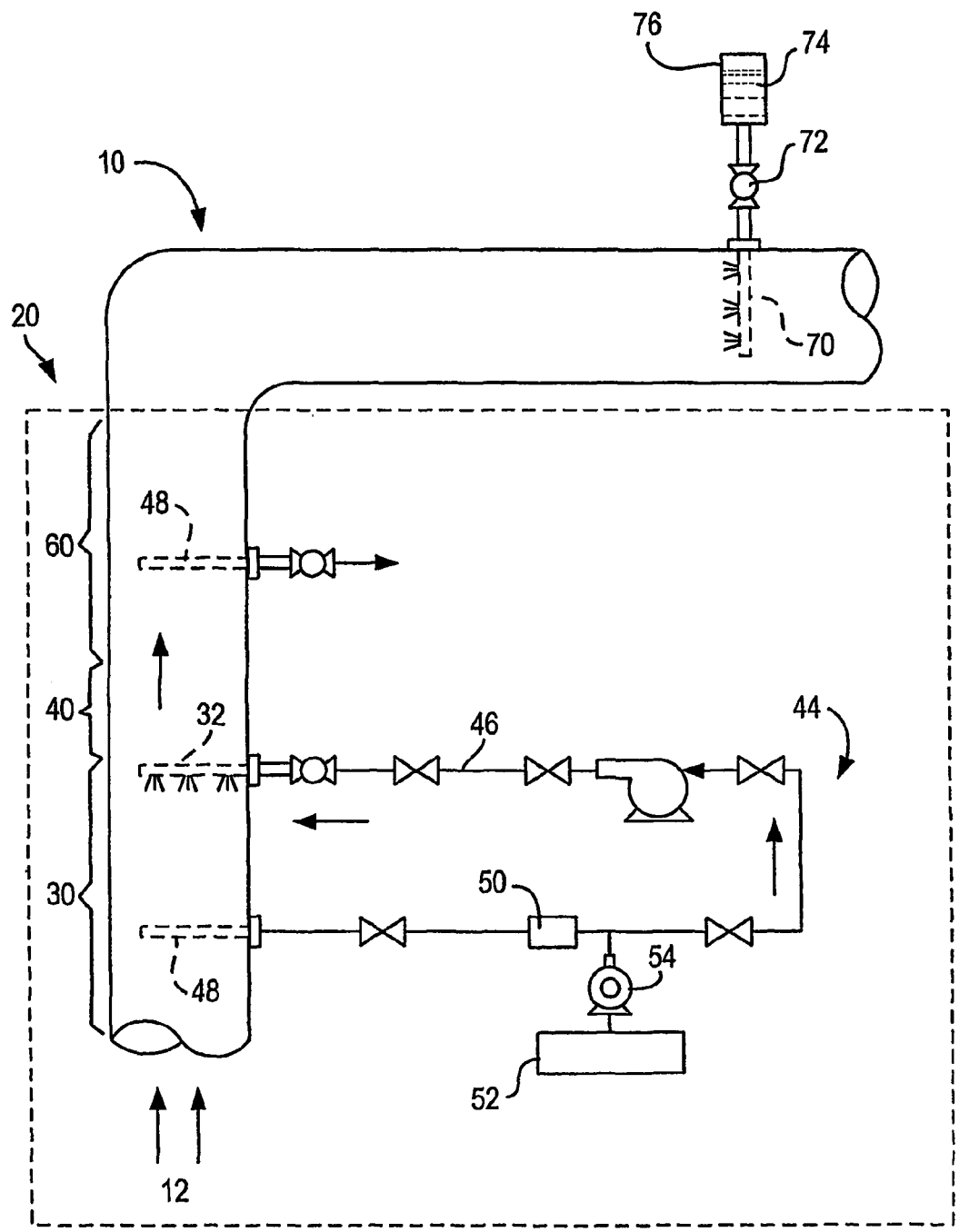
FIG. 2 is a schematic illustration of a second preferred embodiment of the invention.

With continuing reference to FIG. 1, the fluid stream 12 with surfactant passes into an optional mixing zone 40 that is provided with one or more mixing means, such as an in-line static mixer 42 or a power mixer of the injection type 44 that will be discussed in conjunction with FIG. 2. One embodiment of the latter type of power mixer is illustrated. A circulation loop 46 employs an intake nozzle 48 for withdrawing a portion of the fluid stream 12. In the embodiment of FIG. 2, the surfactant foaming agent is added from storage tank 52 by metering pump 54. A densitometer 50 can optionally be included to provide information as to the homogeneity of the foam. The densitometer should have a rapid scan time.

In the embodiment of FIG. 1, the mixing zone 40 and sampling zone 60 are positioned in a vertical section of the pipeline. The sampling probe is preferably mounted in the center one-third portion of the vertical pipe. However, the location of the mixing and sampling zones in a horizontal portion of the pipeline for reasons of convenience is also within the scope of the invention.

The invention also contemplates creating stable foams having a long lifetime which pass through the pipeline to prevent condensation from forming downstream of the sampling zone. The effect of the long life foam is to provide corrosion resistance. However, the addition of a foam breaker must be anticipated as a necessary step to the eventual use of the fluid stream. Thus, with further reference to FIG. 2, a downstream foam breaker distribution nozzle 70 controlled by valve 72 can be utilized to introduce a defoaming composition 74 from reservoir 76. In this regard, consideration of the effect of the surfactants and foam-breaking compounds and/or compositions on downstream uses must also be taken into account.

In one application of the invention following pre-treatment at the well head and prior to separation, typical gas stream conditions can average about 1000 psi with temperatures ranging from 90° F. to 155° F. Water content can be 5% or more, and the fluid stream can contain up to 20% of hydrocarbon condensates. Under these conditions, an anionic surfactant is preferred for producing a high quality foam having a long half-life, good stability and high viscosity.

Stable foams having a long life permit the efficient transmission of wet hydrocarbon gas or gas liquid in pipelines. Where the transmission distance warrants, the foam can be regenerated at one or more regeneration zones. Creation of a fine pore foam will permit efficient pumping of the multiphase fluid.

In a further preferred embodiment, the invention is employed to provide enhanced corrosion protection for pipelines. A foam plug is produced that contains one or more corrosion inhibitors that moves through the pipeline. Because all of the components in the pipeline are contained in each bubble of foam downstream of the mixing zone, the moving foam plug provides a highly-efficient means for applying the corrosion inhibitor(s) to all of the interior surfaces of the pipeline. Furthermore, as the foam plug moves against the resistance of the surface of the pipe, movement of foam particles from the interior to the exterior of the plug occurs, thereby providing fresh foam containing corrosion inhibitor to wet the interior surface of the pipe. This represents a significant improvement over the methods of the prior art where the corrosion inhibitor has a tendency to condense out and move to the lower portion of the pipe where it settled in low spots, traps and the like.

Homogenization of flow is used to ensure that the flow regime is always known and that the constituents representative of that flow regime can be sampled. Additionally, when the flow is homogenized before being measured, the phase velocities are equal, and the density of the mixture is the same over the cross-section of the pipe. The invention reduces the number of and difficulties associated with the measurements required and provides the following additional benefits:

1. Custody Transfer—Recovery of Lost BTU Value at Sales Point

When vaporized, gas condensate liquids are several hundred times the equivalent volume of the liquid form. Even microscopic amounts of hydrocarbon aerosol droplets have a significant impact on gas composition and sales price. In natural gas pipelines, these liquids can exist as pools, films, small droplets or aerosol droplets. These liquids are in a constant state of change as a result of internal pipe or vessel geometrics and gas velocities. Homogenizing the liquids into single-phase natural gas foam permits uniform sampling of gases and liquids and permits the qualification and inclusion of the otherwise lost heating values of the separated liquids.

2. Custody Transfer—Allocation Measurement

Separation and conditioning of liquid and gas streams will be unnecessary for custody transfer measurement allocation. Direct measurement provides stream quantification and cost savings in joint venture installations, where producer allocation is needed prior to combining streams for transportation to a common processing facility.

3. Wet Gas Production—Oil Gas Separation Determination

Multi-phase flow meters are increasingly used for well testing and allocation measurement. In order to optimize the production and gas field life, operators need to be able to regularly monitor the output of each well in the field. The conventional approach is to use a test separator. Test separators are expensive, occupy a lot of space and require a long time to monitor each well because a stabilized pattern is required. In addition, test separators are only moderately accurate (typically ±5 to 10% of each phase flow rate) and cannot be used for continuous well monitoring. A multi-phase meter in combination with the multi-phase sampling system of the invention replaces the test separator by sampling a homogenous stream sample and uses equation of state calculations in conjunction with chromatographic analysis to establish aqueous, liquid and gas phases. Karl Fischer titration for gas systems can be utilized to determine water content.

4. Wet Gas Production—Immediate Determination of Gas Stream Value.

Separation and conditioning of liquid and gas streams will not be necessary to establish the value of the gas stream at the wellhead. Direct measurement of the homogenized liquid-gas flow will provide direct stream quantification.

5. Wet Gas Production—Improved Wet Gas Meter Efficiency

A major obstacle to multi-phase metering is that addition of liquids to the flowing fluids changes several of the flow characteristics, e.g., density and differential pressure. Also, since meters are calibrated on dry gas, they inaccurately record the flow rate of wet gas, unless compensation is made for these changes. The degree of mixing between the gas and liquid also affects the meter creating questions if the fluid is accumulating in pools or condensing on the pipe walls. This accumulation of fluids affects meter accuracy. An homogenized process stream will create constant density under stable process flows and minimize density and flow profile changes under ganging process conditions. This will improve measurement performance of multi-phase meters since flow profile distortion from entrained liquids is reduced or eliminated. Additionally, homogenized multi-phase flow will allow calibration of multi-phase meters on wet flow.

6. Corrosion Protection—Enhanced Corrosion Inhibitor Application

Liquid accumulation and intermittent slug flow in pipelines increase corrosion. Homogenizing a multi-phase stream provides corrosion protection through two mechanisms: reduced contact time of liquids with piping and through uniform coating of corrosion inhibitor products along the piping walls. Some surface active agents to be included in testing are also corrosion inhibitors. Alternatively foaming agents blends can include corrosion inhibitor addictiveness as part of the formulation.

7. Transmission Pipeline—Pumping Efficiency Benefits

The present invention also comprehends a method of applying a liquid, which can be a corrosion inhibitor, to provide a pipeline coating. the benefits include reducing pressure loss in natural gas pipelines by forming a thin film of liquid at the wall. Small amounts of liquid added to a gas in a rough pipeline can increase flow capacity for turbulent flow. Application of a drag reducer at the first point in a pipeline and monitoring the gas flow rate at a second point is utilized to control the amount of drag reducer to maximize the gas rate. As used herein, the term "drag reducer" includes all liquid compositions and compounds that will increase the volumetric flow rate without changing the stream composition. At the pipe wall of a high pressure natural gas pipeline a stable liquid film is created which can reduce pressure loss as great as 15-20%.

Other modifications and variations to the method and apparatus will be apparent from the above description and the full scope of the invention is to be determined with reference to the claims.

I claim:

1. A method for performing analysis on a homogeneous sample of a pressurized multi-phase fluid stream flowing in a pipeline, the fluid stream consisting of a majority component of hydrocarbon gas, the minor component consisting of a minor proportion of one or more hydrocarbon liquids and water in the form of vapor, aerosols, droplets and/or liquid streams, the method comprising:
   a. injecting one or more surface active agents ("saa") into the fluid stream in an injection zone at a rate that is sufficient to form a stable uniform foam of the gas and the one or more hydrocarbon liquids and water components;
   b. mixing the one or more saa with the fluid stream in a mixing zone to form a uniform foam composition flowing in the pipeline downstream of the mixing zone;
   c. withdrawing a portion of the foam composition from the pipeline at a sampling point;
   d. passing the portion of the foam composition withdrawn from the pipeline through a sampling loop that is in communication with the pipeline;
   e. removing a homogeneous sample of predetermined volume of the foam from the sampling loop for compositional analysis; and
   f. performing multiphase analysis on the foam.

2. The method of claim 1, wherein the mixing zone includes mixing means selected from the group consisting of in-line static mixers, injection jets, strainers, screens, Y-strainers, pressure change regions, pumps, piping bends, valves, metering stations, compressors, and combinations thereof.

3. The method of claim 1 which includes the further step of analyzing the homogeneous sample to determine the relative proportions of hydrocarbon gas, hydrocarbon liquid and water content.

4. The method of claim 1 which includes the further step of placing the homogeneous sample in a sample container for subsequent analysis.

5. The method of claim 4, wherein the homogeneous sample is analyzed by an automated in-line analysis apparatus.

6. The method of claim 1, wherein the foam composition is withdrawn from the pipeline through a sampling probe.

7. The method of claim 1, wherein the foam composition is withdrawn from the pipeline at the sampling point by pumping.

8. The method of claim 1, wherein the pipeline is a commercial gas transmission pipeline and the sampling point is located in a portion of the pipeline where the custody for the flowing fluid stream is transferred from a first party to a second party.

9. The method of claim 1 which includes the further step of injecting a defoaming composition into the flowing fluid downstream of the sampling point.

10. The method of claim 1 which includes passing the foam composition through a flow meter that is in fluid communication with the sampling loop.

11. The method of claim 1, wherein the one or more surface active agents is selected from the group consisting of fluorocarbon, cationic, anionic and non-ionic compounds.

12. The method of claim 11, wherein the one or more surface active agents are selected from the group consisting of alkyl sulfonates, including linear $C_{16-18}$ alpha-olefin sulfonate; alkyl aromatic sulfonates; di-sulfonates; alkyl and alkyl-aryl sulfonates including $C_{15-18}$ alkyl-toluene sulfonates; fluorocarbon/hydrocarbon blends;

fluorinated alkyl esters; alcohol sulfates; alcohol ether sulfates; alcohol ethoxylate having $C_{9-11}$, $C_{12-15}$, $C_{12-13}$, and $C_{14-15}$ alkyl groups; alcohol ethoxyglycerl sulfonate having $C_{9-11}$ and $C_{12-15}$ groups; octylphenol ethoxyethyl sulfonate with a $C_8$ alkyl group; nonylphenol ethoxyacetate with a $C_9$ alkyl group; carboxymethylhydroxy propyl/guar polymer gel; ethoxylated alcohols; ethoxylated sulfates, including their sodium and ammonium salts; ethoxylated nonylphenols; ethoxylated alkyl phenols; alkanolamides; ethoxylated fatty acids; glycerol ester hydrotropes; amine oxides; lauryl sulfates; mono and diglycerides; betaine-derived compounds; phosphate esters; quaternnary compounds; sorbitan derivatives; dodecylbenzene sulfonic acid; perfluoro compounds; perfluorooctanylbutane sulfonate; and mixtures of these compounds.

13. The method of claim 1, wherein the pressure and temperature of the foam composition in the sampling loop and the pipeline are substantially the same.

14. The method of claim 4, wherein the pressure of the foam composition in the sample container at the time of filling the container is the same as the pressure in the sampling loop.

15. The method of claim 1 where the injection and mixing zones are the same.

16. The method of claim 1, wherein the foaming agent includes a component for creating caustic conditions.

17. The method of claim 1, wherein the homogeneous sample is used for determining the value of the fluid stream at a custody transfer point.

18. The method of claim 1, wherein the homogeneous sample is used for determining the composition of the fluid stream downstream of a well head.

* * * * *